United States Patent [19]

Chiu et al.

[11] Patent Number: 5,280,122

[45] Date of Patent: Jan. 18, 1994

[54] RESOLUTION OF 2-BENZYL-4-PIPERIDONE-SUCCINIC ACID

[75] Inventors: Charles K. Chiu, Pawcatuck; Morgan Meltz, Niantic, both of Conn.

[73] Assignee: Pfizer Inc., New York, N.Y.

[21] Appl. No.: 907,001

[22] Filed: Jul. 1, 1992

[51] Int. Cl.⁵ .......................................... C07D 211/22
[52] U.S. Cl. .................................................... 546/221
[58] Field of Search ................ 562/401, 402; 546/271

[56] References Cited

U.S. PATENT DOCUMENTS 4,845,272  7/1989  Nohira et al. ........................ 562/401

FOREIGN PATENT DOCUMENTS

438233A2  7/1991  European Pat. Off. .

OTHER PUBLICATIONS

Harada et al., *J. Org. Chem*, 55, 1679–1682 (1990).

*Primary Examiner*—C. Warren Ivy
*Assistant Examiner*—Raymond Covington
*Attorney, Agent, or Firm*—Peter C. Richardson; Paul H. Ginsburg

[57] ABSTRACT

This invention relates to a process for resolving racemic or optically enriched 2-benzyl-4-piperidone-succinic acid, comprising reacting such compound with (+)-cis-N-benzyl-2-(hydroxymethyl)-cyclohexylamine, (−)-cis-N-benzyl-2-(hydroxymethyl)-cyclohexylamine or (+)-dehydroabietylamine.

11 Claims, No Drawings

RESOLUTION OF 2-BENZYL-4-PIPERIDONE-SUCCINIC ACID

BACKGROUND OF THE INVENTION

This invention relates to novel processes for the resolution of racemic or optically enriched 2-benzyl-4-piperidone succinic acid, which has the chemical formula

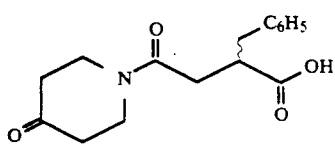

The (2R)-enantiomer of 2-benzyl-4-piperidone-succinic acid, which has the absolute stereochemistry depicted below,

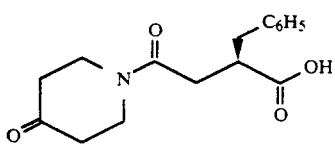

is an intermediate in the synthesis of a compound having the formula

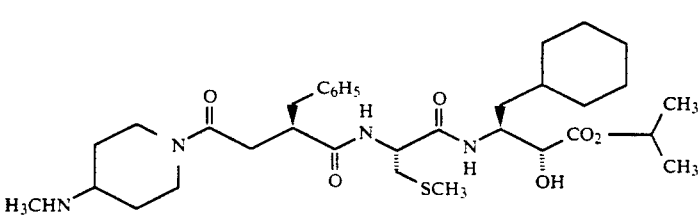

The above compound of formula I exhibits the ability to inhibit the angiotensinogencleaving activity of renin and is useful in the treatment of hypertension and congestive heart failure. Such compound and related peptides that exhibit activity as renin inhibitors are referred to in European Patent Application EP 0438233A2, published on Jul. 24, 1991. The aforesaid publication, is incorporated herein by reference in its entirety.

Methods by which (2R)-2-benzyl-4-piperidone-succinic acid can be converted into the above compound of formula I and related peptides that exhibit activity as renin inhibitors are described in Published European Patent Application EP 0438233A2, referred to above.

Harada et al., *J. Org. Chem.*, 55, 1679–1682 (1990) refer to a method of preparing (2R)-2-benzyl-4-morpholine-succinic acid, which has the chemical formula

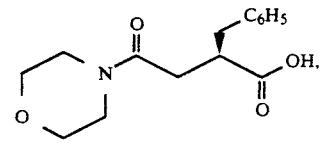

by reacting the corresponding racemic compound with (S)-methyl mandelate, separating the resulting diastereomeric esters, and then hydrolyzing the ester having the "2R" configuration. They also report that attempts to resolve 2-benzyl-4-morpholinosuccinic acid with a wide range of chiral amines were unsuccessful.

SUMMARY OF THE INVENTION

The present invention relates to a process for resolving racemic or optically enriched 2-benzyl-4-piperidone-succinic acid, comprising reacting such compound with (+)-cis-N-benzyl-2-(hydroxymethyl)-cyclohexylamine or (−)-cis-N-benzyl-2-(hydroxymethyl)-cyclohexylamine.

The present invention also relates to a process for preparing a compound having the formula

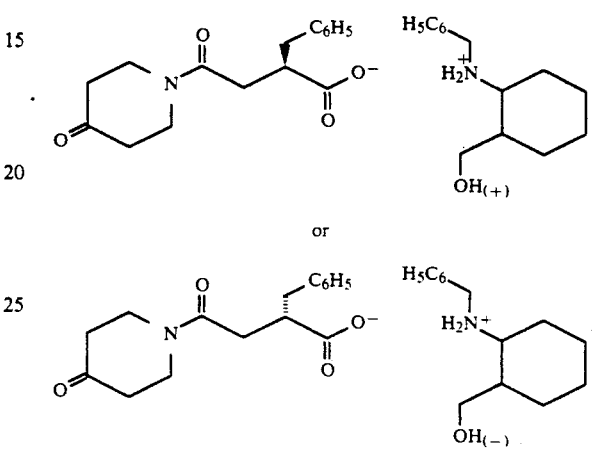

comprising reacting a compound of the formula

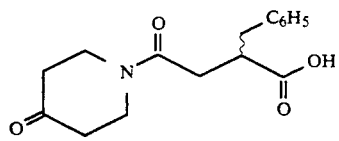

with, respectively, (+)-cis-N-benzyl-2-(hydroxymethyl)-cyclohexylamine or (−)-cis-N-benzyl-2-(hydroxymethyl)-cyclohexylamine.

The present invention also relates to a process for resolving racemic or optically enriched 2-benzyl-4-piperidone-succinic acid, comprising reacting such compound with (+)-dehydroabietylamine.

The present invention also relates to a process for preparing a compound of the formula

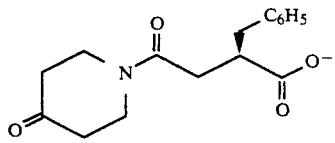

-continued

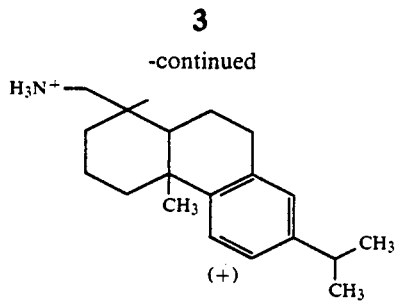

comprising reacting a compound of the formula

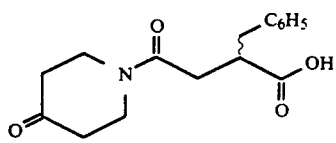

with (+)-dehydroabietylamine.

The present invention also relates to any of the foregoing processes, further comprising hydrolyzing the resulting diastereomeric salt to obtain either(2R)-2-benzyl-4-piperidone-succinic acid or (2S)-2-benzyl-4-piperidone-succinic acid.

Preferably, the foregoing processes are conducted in a solvent selected from acetone, acetonitrile, ethanol, ethyl acetate, isopropyl alcohol and methyl ethyl ketone.

The preferred resolving agents are (+)-cis-N-benzyl-2-(hydroxymethyl)cyclohexylamine and (−)-cis-N-benzyl-2-(hydroxymethyl)-cyclohexylamine. The preferred solvents for this resolving agent are acetone and acetonitrile, with acetone being more preferred.

The preferred solvent for resolutions carried out using (+) -dehydroabietylamine is acetone.

The present invention also relates to a compound having the formula

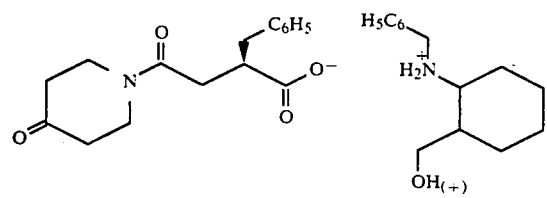

or

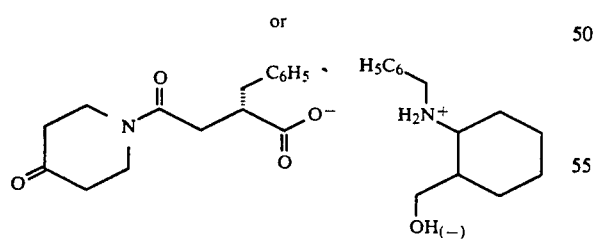

The present invention also relates to a compound having the formula

-continued

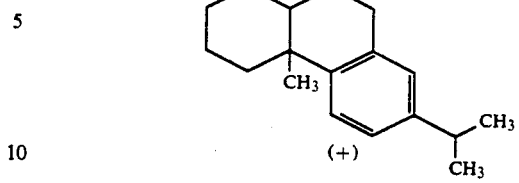

DETAILED DESCRIPTION OF THE INVENTION

The novel processes of this invention are depicted in the following reaction scheme.

SCHEME

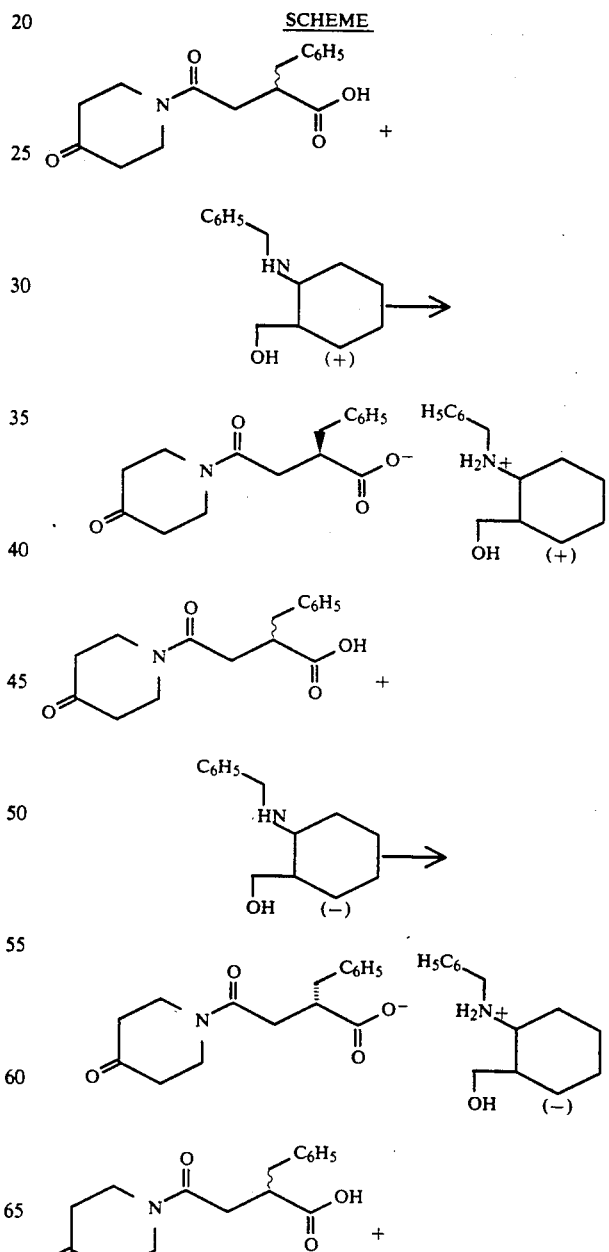

-continued
SCHEME

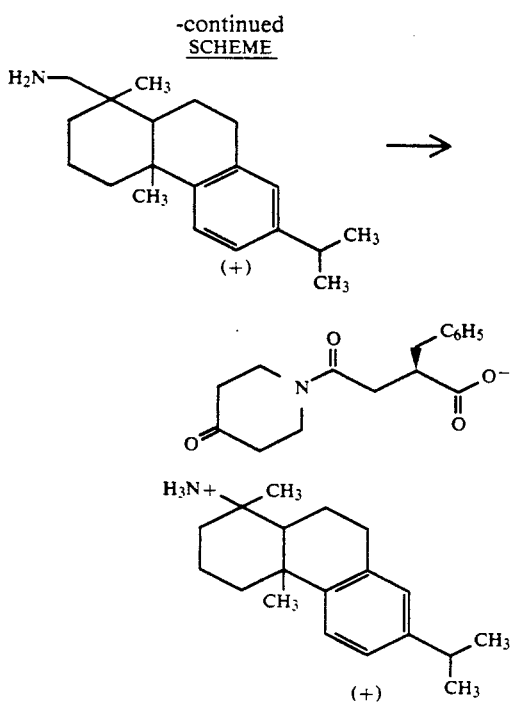

In carrying out the resolution processes of this invention, racemic or optically enriched 2-benzyl-4-piperidone-succinic acid is combined with (+)-cis-N-benzyl-2-(hydroxymethyl)-cyclohexylamine, (−)-cis-N-benzyl-2-(hydroxymethyl)-cyclohexylamine or (+)-dihydroabiethylamine in an appropriate solvent. The mixture is generally heated to achieve complete dissolution. Such processes may be conducted in any solvent capable of dissolving the reactants, including but not limited to those solvents referred to above (i.e., acetone, acetonitrite, ethanol, ethyl acetate, methyl ethyl ketone and isopropanol).

Hydrolysis of the diastereomeric salts obtained using the novel processes of this invention to yield either (2R)-2-benzyl-4-piperidone succinic acid or (2S)-2-benzyl-4-piperidone succinic acid may be carried out using methods that will be obvious to those skilled in the art.

The procedures by which (2R)-2-benzyl-4-piperidone-succinic acid can be used to prepare the renin inhibiting compound having formula I and related renin inhibiting peptides are set forth in European Patent Application EP 0438233A2, published on Jul. 24, 1991, which application is incorporated herein by reference in its entirety.

The renin inhibiting compound having formula I and the related renin inhibiting peptides that can be synthesized using the methods of this invention are useful in the treatment of hypertension and congestive heart failure in animals, including humans.

U.S. patent application Ser. No. 638,238 now abandoned and Published European Patent Application EP 0438233A2, referred to above, sets forth in detail the appropriate dosage ranges and methods of administration of such therapeutic compounds. The aforesaid reference sets forth a method by which the renin inhibiting activity of such compounds may be determined.

The following examples illustrate the methods and compounds of the present invention. It will be understood, however, that the invention is not limited to the specific details of these examples.

EXAMPLE 1

Resolution of 2-Benzyl-4-piperidone-succinic Acid with (+)-cis-N-benzyl-2-(hydroxymethyl)-cyclohexylamine In Acetonitrile A mixture of 2-benzyl-4-piperidone-succinic acid (316 mg, 1.09 mmol) and (+)-cis-N-benzyl-2-(hydroxymethyl)-cyclohexylamine (240 mg, 1.09 mmol) in acetonitrile (2.5 mL) was heated under reflux until complete dissolution. The resulting solution was seeded with a crystal of chiral salt and allowed to cool with magnetic stirring. After 2 hours, the precipitated solid was collected by filtration, washed with acetonitrile and dried in a vacuum oven at 45° C. overnight. Two hundred ten milligrams of dried white solid was obtained (76% yield).

The above white solid salt (118 mg) was recrystallized by dissolving in acetonitrile (1 mL) with heating, and then cooled for over 3 hours with magnetic stirring. The resulting white solid was collected by filtration, washed with acetonitrile and dried in a vacuum oven at 50° C. for 2 days. The dried white solid weighed 75 mg (64% yield), which represents 48% yield for the overall resolution. The salt was analyzed by chiral HPLC and found to have a diastereomeric ratio of 96:4 and e.e. (enantiomeric excess) of 92%.

EXAMPLE 2

Resolution of 2-Benzyl-4-piperidone-succinic Acid In Ethyl Acetate

A mixture of 2-benzyl-4-piperidone-succinic acid (297 mg, 1.03 mmol) and (+)-cis-N-benzyl-2-(hydroxymethyl)-cyclohexylamine (225 mg, 1.03 mmol) in ethyl acetate (3 mL) was heated under reflux and more ethyl acetate (3 mL) was added to complete dissolution. The mixture was allowed to cool and seeded with a crystal of chiral salt as solid gradually precipitated out. The solid was collected by filtration, washed with ethyl acetate and dried in a vacuum oven at 50° C. for 4 hours. Two hundred twenty-eight milligrams of dried white solid was obtained (87% yield).

The above white solid (140 mg) was warmed and dissolved in ethyl acetate (2.5 mL), and then allowed to cool down with stirring. The precipitated white solid was collected by filtration, washed with ethyl acetate and dried in a vacuum oven at 50° C. for 4 hours. The dried salt weighed 101 mg (72% yield) and represents 63% yield for the overall resolution. The salt was analyzed by chiral HPLC and found to have a diastereomeric ratio of 90:10 and an e.e. of 80%.

EXAMPLE 3

Resolution of 2-Benzyl-4-piperidone-succinic Acid In Methyl Ethyl Ketone

A mixture of 2-benzyl-4-piperidone-succinic acid (305 mg, 1.05 mmol) and (+)-cis-N-benzyl-2-(hydroxymethyl)-cyclohexylamine (231 mg, 1.05 mmol) was dissolved in methyl ethyl ketone (3 mL) with heating. The resulting mixture was cooled with stirring for over 3 hours. The precipitated white solid was collected by filtration, washed with methyl ethyl ketone and dried in a vacuum oven at 50° C. for 2 days. Two hundred twenty-two milligrams of dried white solid was obtained (83% yield).

The above white solid (171 mg) was recrystallized by dissolving in methyl ethyl ketone (2.2 mL) with warming and then allowed to cool with stirring for over 2 hours. The precipitated solid was collected by filtration, washed with methyl ethyl ketone and dried in a vacuum oven at 50° C. overnight. The dried salt weighted 120 mg (70% yield) and represents 50% overall yield for the resolution. The salt was analyzed by chiral HPLC and found to have a diastereomeric ratio of 88:12 and an e.e. of 76%.

EXAMPLE 4

Resolution of 2-Benzyl-4-piperidone-succinic Acid In Isopropanol

A mixture of 2-benzyl-4-piperidone-succinic acid (274 mg, 0.95 mmol) and (+)-cis-N-benzyl-2-(hydroxymethyl)-cyclohexylamine (208 mg, 0.95 mmol) was heated in isopropanol (3 mL) to complete dissolution. The resulting mixture was seeded with a crystal of chiral salt and allowed to cool. White solid crashed out of solution within an hour and was collected and washed with isopropanol. After drying in a vacuum oven at 45° C. overnight, 179 mg of white solid (74%) as obtained. The optical purity of the salt was found to be 70% e.e. (diastereomeric ratio=85:15) by chiral HPLC assay.

EXAMPLE 5

Resolution of 2-Benzyl-4-piperidone-succinic Acid in Ethanol

A mixture of 2-benzyl-4-piperidone-succinic acid (396 mg, 1.37 mmol) and (+)-cis-N-benzyl-2-(hydroxymethyl)-cyclohexylamine (300 mg, 1.37 mmol) was dissolved in ethanol (1.5 mL) with heating. The resulting mixture was allowed to cool and seeded with a crystal of chiral salt. White solid precipitated out and was collected by filtration, washed with ethanol, and then dried in a vacuum oven at 50° C. for 4 hours. Two hundred twelve milligrams of dried white solid was obtained and the optical purity was found to be 48% e.e. (diastereomeric ratio=69:21) by chiral HPLC assay.

EXAMPLE 6

Resolution of 2-Benzyl-4-piperidone-succinic Acid with (+)-Dehydroabietylamine In Acetone A solution of (+)-dehydroabietylamine (548 mg, 1.92 mmol) in acetone (15 mL) was treated with 2-benzyl-4-piperidone-succinic acid (555 mg, 1.92 mmol) and heated with stirring until complete dissolution. The resulting mixture was allowed to cool and solid precipitated out. The solid was collected by filtration, washed first with acetone, and then with hexane, and then sucked dry on the filtration funnel. Three hundred seventy-five milligrams (88% yield) of solid was obtained and the optical purity was found to be 66% e.e. (diastereomeric ratio=83:17) by chiral HPLC assay.

The above solid (330 mg) was recrystallized by dissolving in acetone (4.5 mL) with heat and then allowed to cool with stirring. The precipitated solid was collected by filtration, washed with acetone and then with hexane, and sucked dry on the filtration funnel. 120 mg (36%) of dry solid was obtained and the optical purity was found to be 92% e.e. (diastereomeric ratio=94:4) by chiral HPLC assay.

EXAMPLE 7

Hydrolysis of the Resolved 2-Benzyl-4-piperidone-succinic acid/(+)-cis-N-Benzyl-2-(hydroxymethyl)-cyclohexylamine Salt The resolved salt (240 mg, 0.47 mmol) was dissolved in a mixture of methylene chloride ($CH_2Cl_2$) (10 mL) and water (10 mL). Five percent aqueous hydrochloric acid was added slowly to the mixture until pH-3.5 was obtained. The aqueous hydrochloric layer was separated and extracted once with $CH_2Cl_2$. The combined $Ch_2Cl_2$ was washed twice with water and then dried over sodium sulfate. Removal of solvent provided 80 mg of the acid (59%).

We claim:

1. A process for resolving racemic or optically enriched 2-benzyl-4-piperidone-succinic acid, comprising reacting such compound with (+)-cis-N-benzyl-2-(hydroxymethyl)-cyclohexylamine or (−)-cis-N-benzyl-2-(hydroxymethyl)-cyclohexylamine.

2. A process for preparing a compound having the formula

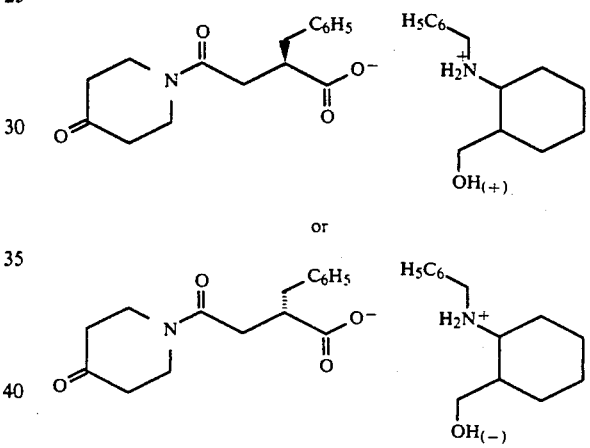

or comprising reacting a compound of the formula

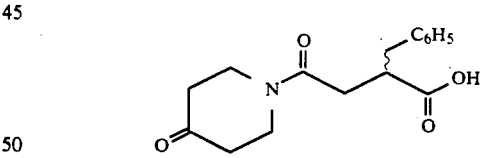

with, respectively, (+)-cis-N-benzyl-2-(hydroxymethyl)-cyclohexylamine or (−)-cis-N-benzyl-2-(hydroxymethyl)-cyclohexylamine.

3. A process according to claim 1, further comprising hydrolyzing the resulting diastereomeric salt to obtain either (2R)-2-benzyl-4-piperidone-succinic acid or (2S)-2-benzyl-4-piperidone-succinic acid.

4. A process according to claim 2, further comprising hydrolyzing the resulting diastereomeric salt to obtain either (2R)-2-benzyl-4-piperidone-succinic acid or (2S)-2-benzyl-4-piperidone-succinic acid.

5. A process according to claim 1, wherein said process is conducted in a solvent selected from acetone, acetonitrile, ethanol, ethyl acetate, isopropyl alcohol and methyl ethyl ketone.

6. A process according to claim 2, wherein said process is conducted in a solvent selected from acetone, acetonitrile, ethanol, ethyl acetate, isopropyl alcohol and methyl ethyl ketone.

7. A process according to claim 5, wherein said process is conducted in an acetone solvent.

8. A process according to claim 5, wherein said process is conducted in an acetonitrile solvent.

9. A process according to claim 6, wherein said process is conducted in an acetone solvent.

10. A process according to claim 6, wherein said process is conducted in an acetonitrile solvent.

11. A compound having the formula

or

* * * * *